United States Patent [19]

Balsells

[11] Patent Number: 4,804,290
[45] Date of Patent: Feb. 14, 1989

[54] LATCHING AND SEALING DEVICE

[75] Inventor: Peter J. Balsells, 17592 Sherbrook Dr., Tustin, Calif. 92680

[73] Assignees: Peter J. Balsells; Joan C. Balsells, both of Santa Ana, Calif.

[21] Appl. No.: 899,165

[22] Filed: Aug. 22, 1986

[51] Int. Cl.[4] .......................... F16B 21/18; F16J 15/24
[52] U.S. Cl. ..................................... 403/326; 403/334;
403/225; 403/361; 403/368; 277/153; 277/164;
285/318; 92/194
[58] Field of Search ............... 403/365, 366, 367, 368,
403/374, 375, 220, 221, 228, 229, 361, 326, 333,
334, 327, 226, 225, 227; 277/152, 153, 164;
92/216, 194, 200; 285/318

[56] References Cited

U.S. PATENT DOCUMENTS

| 894,091 | 7/1908 | Williams | 92/194 |
|---|---|---|---|
| 2,101,346 | 12/1937 | Robertson | 308/184 |
| 2,154,275 | 4/1939 | Linn | 248/358 |
| 2,538,683 | 1/1951 | Guiler et al. | 285/163 |
| 2,797,937 | 7/1957 | Frishof | 285/105 |
| 2,814,540 | 11/1957 | Sontherwick | 92/194 |
| 2,819,063 | 1/1958 | Neidhart | 403/228 X |
| 2,846,240 | 8/1958 | Beyer | 285/318 X |
| 2,886,355 | 5/1959 | Wurzel | 403/326 |
| 2,890,072 | 6/1959 | Kaman et al. | 403/365 |
| 2,973,231 | 2/1961 | Reynolds | 92/194 X |
| 2,999,707 | 9/1961 | Kniepkamp et al. | 403/361 X |
| 3,250,331 | 5/1966 | Boyle | 166/133 |
| 3,315,537 | 4/1967 | Keller | 403/225 X |
| 3,359,617 | 12/1967 | Baumler | 29/173 |
| 3,377,075 | 4/1968 | Feller | 277/149 |
| 3,762,726 | 10/1973 | Jornhagen | 277/153 X |
| 3,782,840 | 1/1974 | Brishka | 403/361 |
| 3,820,739 | 6/1974 | Graf | 403/225 X |
| 3,910,566 | 10/1975 | Pedersen et al. | 267/167 |
| 4,142,543 | 3/1979 | Krause et al. | 403/326 X |
| 4,172,599 | 10/1979 | Forch | 277/153 |
| 4,304,414 | 12/1981 | Forch | 277/153 |
| 4,630,958 | 12/1986 | McCallister | 403/326 X |
| 4,655,462 | 4/1987 | Balsells | 277/164 |
| 4,678,210 | 7/1987 | Balsells | 285/318 |

FOREIGN PATENT DOCUMENTS

| 92468 | 10/1959 | Netherlands | 277/153 |
|---|---|---|---|
| 300074 | 1/1968 | Sweden | 277/153 |
| 742211 | 12/1955 | United Kingdom | 277/153 |

Primary Examiner—Andrew V. Kundrat
Assistant Examiner—Peter M. Cuomo
Attorney, Agent, or Firm—Walter A. Hackler

[57] ABSTRACT

A latching and sealing device suitable for use as a cover seal for a plunger or piston in a syringe or plunger pump includes a cylindrical seal member having a body portion and lip-and-latch means for both sealably engaging a surrounding surface and latching to the piston. A spring disposed in between the lip-and-latch means and the piston provide a constant sealing pressure while allowing the piston and seal member to be moved within a bore. Sealing between the lip-and-latch means and the bore is enhanced by use of a berm and notches radially aligned with the biasing spring.

18 Claims, 2 Drawing Sheets

LATCHING AND SEALING DEVICE

The present invention generally relates to seals for cylindrical members and is more particularly directed to seals for use in plunger tips, specifically those in which the sealing device must also be latched, or locked, to a cylindrical piston, such as in syringe pumps and reciprocating plunger pumps.

The engagement of lightweight, delicate and many times fragile, cylindrical parts of laboratory equipment useful in chemical analysis, particularly in the hematology, pathology and biochemical fields, often requires a seal which must be locked to a piston or the like, in order that it is not separated therefrom during movement thereof.

Many of these devices must limit the exposure to biological fluids to acceptable material, such as PTFE and glass, while at the same time be simple and inexpensive. In addition, reliability of both the seal and the latching of the seal to the piston must be assured in order that equipment malfunction does not occur, such as seepage or leakage of biological fluids past the seal.

Because of variations of dimensions in the bore diameters into which the seal and piston are to be used such as is common in glass tubes, seals heretofore have generally utilized devices incorporating forces far in excess of that necessary for creating the seal. That is, heretofore, to accommodate for variation in bore diameters, excess sealing forces have been used. This has a disadvantage in that additional excess pressure, or force, must be borne by the contacted surfaces which can provide unwanted loading on both the piston and the surfaces being sealed.

The latching and sealing device of the present invention provides for a seal for use with a piston wherein a seal is provided between the piston and a surrounding glass tube which is relatively constant and independent of variations on the glass tube bore diameter. Further, the present invention has the feature of the seal itself, providing a latching, or locking, function with the piston in order to facilitate movement of the piston within a glass tube. The sealing device of the present invention is suitable for pumps used in fast protein liquid chromatography where the typical pressure range is from about 15 psi (1 Bar) to about 1500 psi (100 Bar) and corrosive solvents such as acetonitrile solutions may be used.

SUMMARY OF THE INVENTION

The latching and sealing device in accordance with the present invention generally includes a cylindrical seal member comprising a body portion and lip-and-latch means flexibly depending from the body portion and adapted for both sealably engaging a surrounding surface and latching to a cylindrical core or piston. The adaption for engaging the surrounding surface incorporated in the lip-and-latch means includes groove means formed on an inside surface of the lip-and-latch means for supporting a spring therein.

A cylindrical core, or piston, is provided which includes means defining a circumferential groove therein for supporting a spring and spring means is disposed between the lip-and-latch means and the cylindrical core and within the lip-and-latch means groove and the circumferential core for both radially forcing the lip-and-latch means into engagement with the surrounding surface and acting in cooperation with the lip-and-latch means groove and the circumferential groove to axially lock, or latch, the cylindrical seal member to the cylindrical core.

The axially locking of the cylindrical seal member and the cylindrical core enables the seal member to be inserted and removed from a bore, or the like, using the cylindrical core alone without requiring any additional apparatus for placement of the seal or insertion or withdrawal thereof separate from the cylindrical core. Preferably, the spring means comprises a continuous torroidal-type spring and the lip-and-latch means further comprises means defining a circumferential berm thereon for concentrating the sealing pressure between the lip-and-latch means and the surrounding surface produced by the torroidal-type spring. To further enhance this sealing function, the circumferential berm is radially aligned with the lip-and-latch groove and the torroidal-type spring.

To facilitate assembly of the device, the cylindrical core may include ramp means for radially compressing the torroidal-type spring to enable assembly of the latching and sealing device outside of the borehole.

Enhanced sealing of the lip-and-latch means to the surrounding surface is provided when notch means are incorporated into the circumferential berm for engaging and sealing with the surrounding surface.

It should be appreciated that flexibility of the lip-and-latch means not only provides for facilitating the transfer of force from the torroidal-type spring to the surface being sealed, but also provides a sealing force itself. Additionally, the flexibility enables assembly of the latching and sealing device. This feature is enabled by the flexibility of the lip-and-latch means being sufficient to radially expand when engaged by the torroidal-type spring during assembly of the latching and sealing device in which the spring is engaged by the ramp with such flexibility being sufficient to enable assembly of the device by compressing the torroidal-type spring into the lip-and-latch groove without exceeding the elastic limit of the torroidal-type spring, which may cause permanent deformation thereof.

Also important in the present invention is the providing of means for both coaxially aligning the cylindrical seal member with the cylindrical core and locating the spring means for engagement with the lip-and latch groove means to enable assembly of the latching and sealing device.

The last mentioned means comprises an end portion of the cylindrical core which has a diameter greater than the inside diameter of the torroidal-type spring in its relaxed condition. This end portion, or tip, of the cylindrical core ensures coaxial alginment of the core and the seal and prevents skewing of the seal within the bore which may detract from its sealing characteristics and hinder movement of the seal and piston. In addition, the end portion facilitates assembly of the device without any separate gigs or handling mechanisms.

In another embodiment of the present invention, the lip-and-latch means includes first and second groove means formed in an inside surface thereof with each of the first and second lip-and-latch groove means being operative for supporting a first and a second spring therein, respectively.

The cylindrical core includes means defining a first and a second circumferential groove therein for supporting the first and second springs therein, respectively, and first and second spring means are provided for radially forcing the lip-and-latch means into engagement with the surrounding surface and acting in cooperation with the first and second lip-and-latch grooves and the first and second circumferential grooves to axially lock the cylindrical seal member to the cylindrical core.

BRIEF DESCRIPTIONS OF THE DRAWINGS

A better understanding of the present invention may be had from consideration of the following detailed description, taken into conjunction with the accompanying drawings, in which:

FIG. 1 is a perspective view of the present invention disposed in a borehole, or the like, partially broken away and generally showing a cylindrical seal member having a body portion and lip-and-latch means along with a cylindrical core and spring means disposed in a lip-and-latch groove and a circumferential groove in the cylindrical core;

FIGS. 2A, B, C, are cross-sectional views of the latching and sealing of the device shown in FIG. 1 showing in a stepwise fashion the assembly of the seal outside of the bore and more particularly showing an end, or tip portion, of the cylindrical core, which provides means for both coaxially aligning the cylindrical seal member with the cylindrical core and locating the spring means for engagement by the lip-and-latch groove; and, FIGS. 3A, B and C, are cross-sectional views of an alternative embodiment of the present invention utilizing two springs and showing assembly of the latching and sealing device assembly procedure.

DETAILED DESCRIPTION

Figure 1:
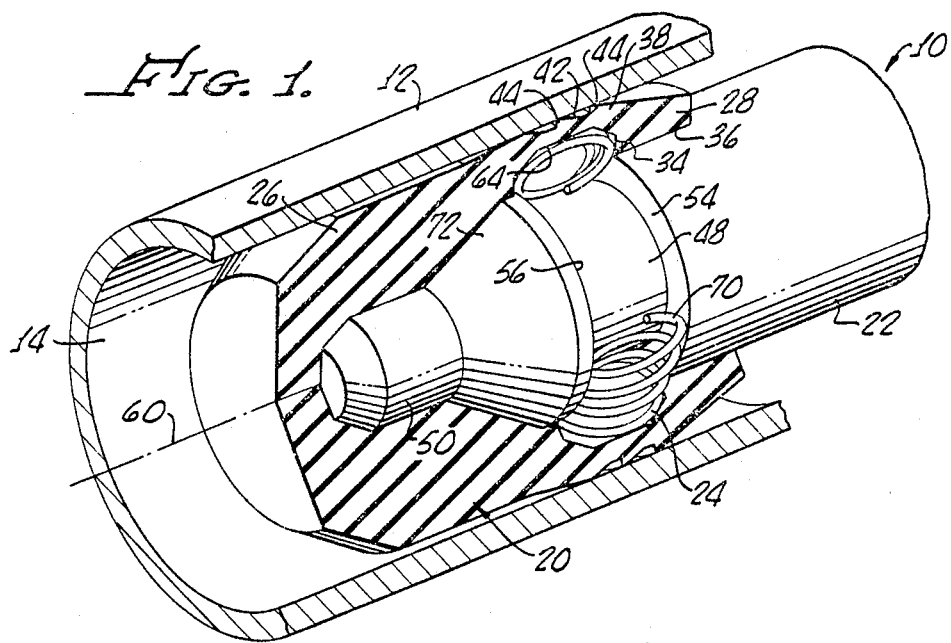

Turning now to FIG. 1, there is shown a latching and sealing device 10 disposed within a glass tube, or bore, 12 having an inside surface 14. Medical or laboratory equipment for which the present invention is intended for use typically utilizes glass tubes having inside diameter of about 0.015 to about 0.020 inches.

Shown in a partially broken perspective view in FIG. 1, the latching and sealing device 10 generally includes a cylindrical seal member 20, a cylindrical core, or piston, 22 and a spring 24.

For use in laboratory equipment, the cylindrical seal member 20 is preferably formed from polytetrafluoroethylene, or the like, and generally consists of a body portion 26 and a lip-and-latch portion 28 which provides means for sealably engaging the surrounding surface 14 and latching the cylindrical seal member 20 to the cylindrical core 22. As hereinafter discussed in greater detail, the lip-and-latch 28 includes a groove 34 formed on an inside surface 36 of the lip-and-latch 28 which provides a means for supporting the spring 24 therein.

The lip-and-latch 28 flexibly depends from the body 26 and the thickness and shape thereof enable the lip-and-latch 28 to exert an outward radial force against the surface 14 and also enable assembly of the latching and sealing device 10 as hereinafter described.

To enhance the sealing between the seal member 20 and the surface 14, a raised portion, or circumferential berm, 38 may be formed on the lip-and-latch which provides means for concentrating the sealing pressure between the lip-and-latch and the surrounding surface 14 produced by the spring 24. In addition, to provide for a supple engagement between the berm 38 and the surface 14, the berm 38 may have notches 42 therein which provide tapered projections 44 on the berm 38 which are easily deformed by the pressure between the lip-and-latch 28 and the surface 14, thereby facilitating the seal therebetween.

The cylindrical core 22 includes a circumferential groove 48 therein which provides means for supporting the spring 24 between the lip-and-latch 28 and the cylindrical core 22.

In addition, the cylindrical core 22 includes an end portion, or tip 50, which provides a means for both coaxially aligning the seal member 20 onto and with the cylindrical core 22 and for locating the spring 24 thereon for engagement by the lip-and-latch groove 34 to enable assembly of the latching and sealing device 10 as hereinafter described. Maintaining alignment between the seal member 20 and the cylindrical core, or piston, 22, is important since skewing of the seal member 20 within the bore 12 jeopardizes the security of the seal therebetween and may inhibit movement of the piston 22.

Axial locking between the seal member 20 and the cylindrical core 22 is ensured by two locking surfaces 54, 56 disposed generally parallel to one another and in planes generally perpendicular to the axis 60 of the cylindrical core 22. Upon assembly of the latching and sealing device 10, the spring 24 snaps into the groove 48 and is prevented from moving thereout of by the locking surfaces 54, 56. This allows the cylindrical core, or piston, to move within the bore 12 while maintaining a seal therebetween through the cylindrical seal member 20. Similarly, an inside surface 64 of the groove 34 prevents a separation of the spring from the lip-and-latch 28. In order to provide constant radial force between the lip-and-latch 28 and the surface 14, the spring 24 may be of a continuous torroidal-type including a plurality of canted coils 70 for providing a constant force over a preselected range of deflection. A full description of this type of spring is set forth in U.S. Pat. No. 4,655,462 issued Apr. 7, 1987, which is incorporated herewith by specific reference thereto.

Figure 2A:
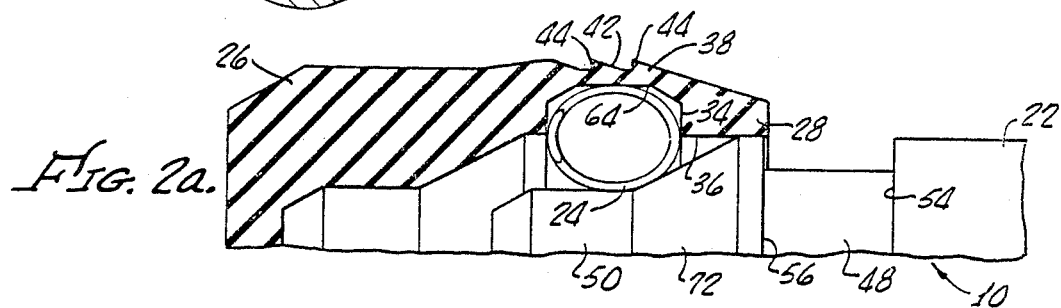
Figure 2B:
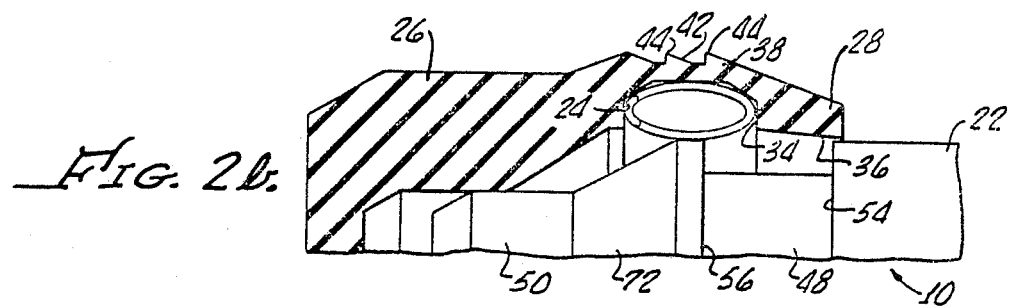
Figure 2C:
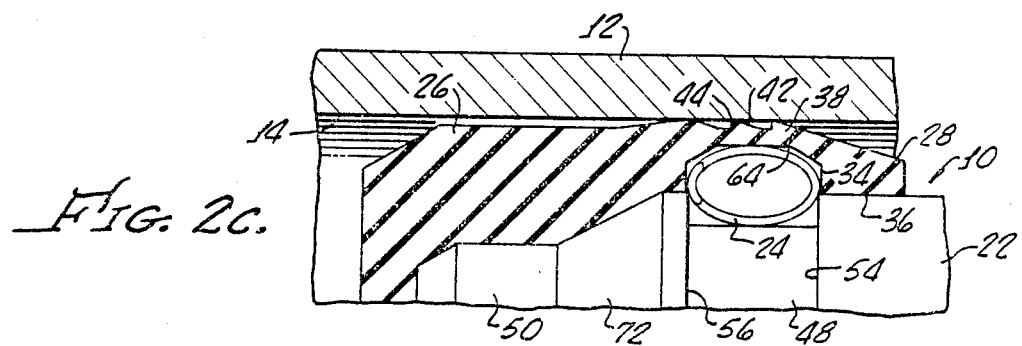

FIGS. 2A, B and C show assembly of the latching and sealing device 10 before insertion into the bore 12. As hereinbefore pointed out, the cylindrical core 22 includes an end portion, or tip, 50 for supporting the spring at 24, as shown in FIG. 2A. It should be appreciated that the diameter of the tip portion 50, which is greater than the inside diameter of the torroidal-type spring 24 when it is in a relaxed condition, in order that the tip 50 slightly expands the spring 24 when in the position as shown in FIG. 2A. In addition, the cylindrical core includes a ramp portion 72 for radially compressing the spring 24 into the groove 34 to enable assembly of the latching and sealing device 10. This compression is more clearly shown in FIG. 2B, which illustrates an intermediate position before the spring reaches its final position, as illustrated in FIG. 2C.

It should be appreciated that the lip-and-latch 28 depending from the body 26 fo the seal member 20 has sufficient flexibility to radially expand, if necessary, when engaged by the spring 24 during assembly of the latching and sealing device 10 in order to enable such assembly without exceeding the elastic limit of the spring 24, thus causing unwanted permanent deformation thereof.

Figure 3A:
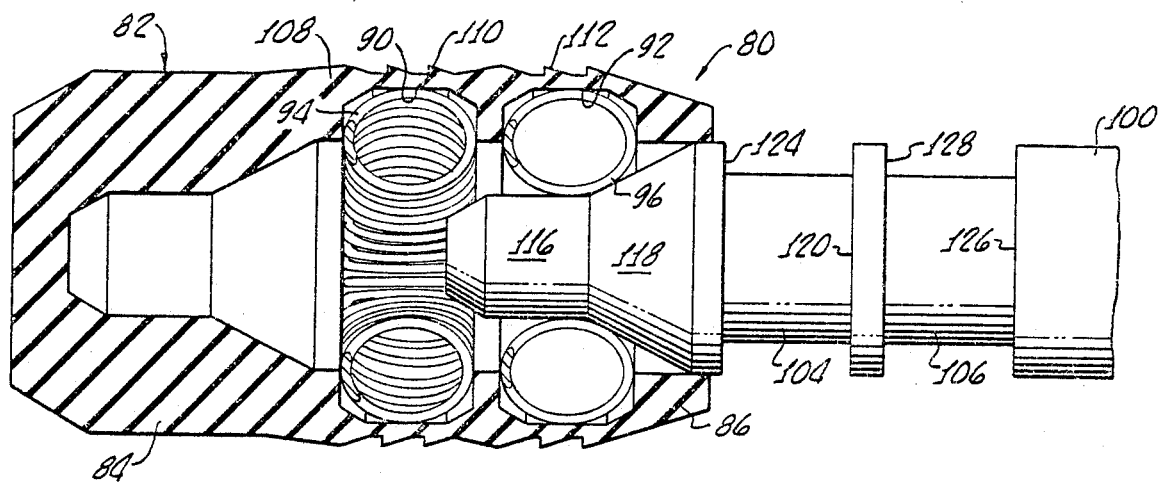
Figure 3B:
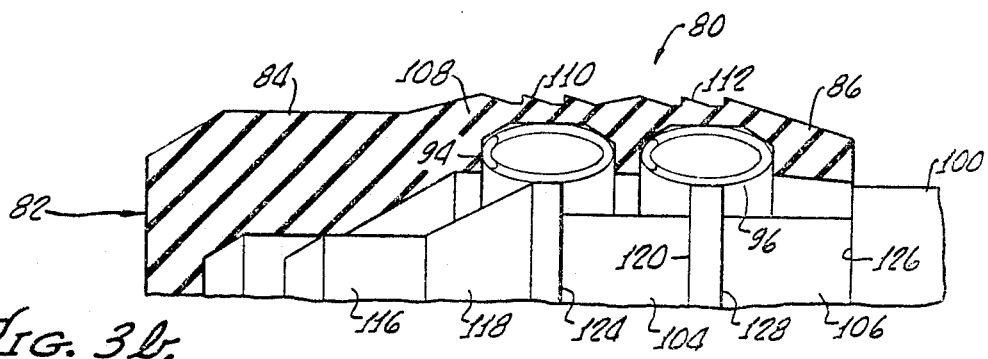
Figure 3C:
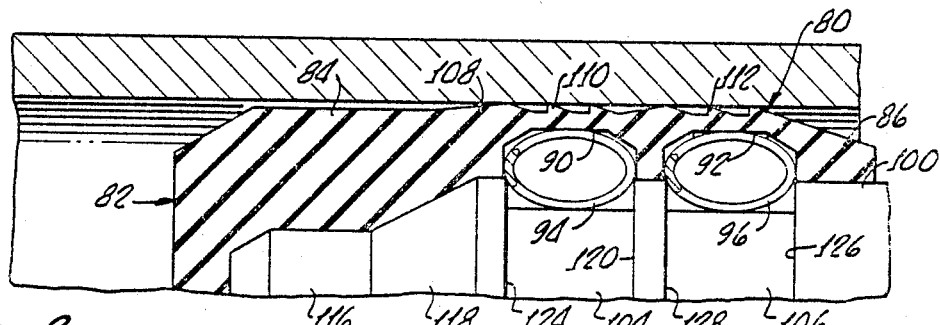

FIGS. 3A, B and C show an alternative embodiment 80 of the present invention in which the latching and sealing device includes a seal member 82 having a body 84 and a lip-and-latch 86, the lip-and-latch having a first and a second groove 90, 92 therein for accommodating a first and a second spring 94, 96.

Similarly, the cylindrical core 100 has first and second circumferential grooves 104, 106 and the berm 108 includes spaced-apart notches 110, 112. The lip-and-latch 86, grooves 90, 92, 104, 106, springs 94, 96 and core 100 as well as the notches 110, 112, operate in a manner as hereinbefore described in connection with the previously described latching and sealing device 10.

The core 100 includes an end portion 116 for both coaxially aligning the cylindrical seal 82 with the core 100 and for locating the first and second spring 94, 96, for engagement by the lip-and-latch grooves 90, 92 during assembly of the latching and sealing device 80. Importantly, the first core groove 104 includes a ramp 118, which provides means for radially compressing the first and second springs 94, 96, as hereinbefore described in connection with the latching and sealing device 10 to enable assembly of the latching and sealing device 80, a locking surfaces 120, 124 in the first core groove 104 and locking surfaces 126, 128 in the second core groove 106 prevent axial movement between the seal member 82 and the core 100 after assembly.

In addition to increasing the amount of available pressure between the seal member 82 and an inside bore surface, not shown, the two spring configuration adds additional locking between the seal member 82 and the core 100. The lip-and-latch 86, having a larger berm 108 thereon, provides for increased surface engagement for sealing than the latching and sealing device 10. Because the seal member 82 is locked to the core 100, it may be placed at any position within a bore and thereafter withdrawn without separation therebetween, thereby enabling the bore to be sealed and unsealed at any preselected location.

Although there has been described hereinabove a specific latching and sealing device in accordance with the present invention for the purpose of illustrating the manner in which the invention may be used to advantage, it should be appreciated that the invention is not limited thereto. Accordingly, any and all modifications, variations, or equivalent arrangements, which may occur to those skilled in the art, should be considered to be within the scope of the invention as defined in the appended claims.

What is claimed is:

1. A latching and sealing device comprising:
a cylindrical seal member comprising a body portion and lip-and-latch means flexibly depending from said body portion and adapted, for both sealably engaging a surrounding surface and latching to a cylindrical core, said lip-and-latch means including groove means formed on an inside surface of said lip-and-latch means for supporting a spring therein;
a cylindrical core including means defining a circumferential groove therein for supporting a spring; and,
spring means disposed between the lip-and-latch means and the cylindrical core, and within the lip-and-latch means groove and circumferential groove, for radially forcing the lip-and-latch means into engagement with a surrounding surface and acting in cooperation with the lip-and-latch means groove and circumferential groove to axially lock the cylindrical seal member to the cylindrical core.

2. The latching and sealing device according to claim 1 wherein said spring means comprises a continuous torroidal-type spring.

3. The latching and sealing device according to claim 2 wherein said lip-and-latch means further comprises means defining a circumferential berm thereon for concentrating the sealing pressure between the lip-and-latch means and the surrounding surface produced by the torroidal-type spring.

4. The latching and sealing device according to claim 3 wherein said circumferential berm is radially aligned with the lip-and-latch groove and the torroidal-type spring.

5. The latching and sealing device according to claim 4 wherein said circumferential berm including notch means for engaging and sealing with the surrounding surface.

6. The latching and sealing device according to claim 5 wherein said cylindrical core includes ramp means for radially compressing said torroidal-type spring to enable assembly of the latching and sealing device with the torroidal-type spring disposed within the lip-and-latch means groove and the circumferential groove in the cylindrical core.

7. The latching and sealing device according to claim 6 wherein said lip-and-latch means has sufficient flexibility to radially expand when engaged by the torroidal-type spring during assembly of the latching and sealing device so that the torroidal-type spring can be compressed into the lip-and-latch groove without exceeding the elastic limit of the torroidal-type spring.

8. The latching and sealing device according to claim 7 further comprising means for both coaxially aligning said cylindrical seal member with said cylindrical core and locating the spring means for engagement by the lip-and-latch groove means to enable assembly of the latching and sealing device.

9. The latching and sealing device according to claim 8 wherein coaxially aligning and spring location means comprises an end portion of said cylindrical core, said end portion having a diameter greater than the inside diameter of the torroidal-type spring in its relaxed condition.

10. The latching and sealing device according to claim 9 wherein said cylindrical groove includes means defining two locking surfaces therein, said locking surfaces being disposed in planes perpendicular to the axis of the cylindrical core, said last mentioned means being operative for preventing separation of the cylindrical seal member and said cylindrical core in an axial direction by engagement of the locking surfaces with the torroidal-type spring 11. A latching and sealing device comprising:
a cylindrical seal member comprising a body portion and lip-and-latch means flexibly depending from said body portion and adapted for both sealably engaging a surrounding surface and latching to a cylindrical core, said lip-and-latch means including first and second groove means formed on an inside surface of said lip-and-latch means, each first and second lip-and-latch groove means being operative for supporting a first and second spring therein, respectively;
a cylindrical core including means defining a first and a second circumferential groove therein for supporting the first and second spring therein, respectively;
first spring means disposed between the lip-and-latch means and the cylindrical core and within the first lip-and-latch groove and the first circumferential groove for radially forcing the lip-and-latch means into engagement with a surrounding surface and acting in cooperation with the first lip-and-latch groove and the first circumferential groove to axially lock the cylindrical seal member to the cylindrical core; and second spring means disposed between the lip-and-latch means and the cylindrical core and within the second lip-and-latch groove and the second circumferential groove for radially forcing the lip-and-latch means into engagement with a surrounding surface and acting in cooperation with the second lip-and-latch groove and the second circumferential groove to axially lock the cylindrical seal member to the cylindrical core.

12. The latching and sealing device according to claim 11 wherein said first and second spring means each comprises a first and second continuous torroidal-type spring, respectively.

13. The latching and sealing device according to claim 12 wherein said lip-and-latch means further comprises means defining a circumferential berm thereon for concentrating the sealing pressure between the lip-and-latch means and the surrounding surface produced by first and second torroidal-type springs.

14. The latching and sealing device according to claim 13 wherein said circumferential berm includes notch means for engaging and sealing with the surrounding surface.

15. The latching and sealing device according to claim 14 wherein said cylindrical core includes ramp means for radially compressing said first and second torroidal-type springs, respectively, to enable assembly of the latching and sealing device with the first torroidal-type spring disposed within the first lip-and-latch groove and first circumferential groove and the second torroidal-type spring disposed within the second lip-and-latch groove and the second circumferential groove.

16. The latching and sealing device according to claim 15 wherein said lip-and-latch means has sufficient flexibility to radially expand when engaged by the first and second torroidal-type springs during assembly of the latching and sealing device so that the first and second torroidal-type spring can be compressed into the first and second lip-and-latch grooves, respectively, without exceeding the elastic limit of the first and second torroidal-type spring.

17. The latching and sealing device according to claim 16 further comprising means for both coaxially aligning said cylindrical seal member with said cylindrical core and locating the first and second spring means for engagement by the first and second lip-and-latch groove means, respectively, to enable assembly of the latching and sealing device.

18. The latching and sealing device according to claim 17 wherein the coaxially aligning and spring locating means comprises an end portion of said cylindrical core, said end portion having a diameter greater than the inside diameter of the first and second torroidal-type spring in its relaxed condition.

* * * * *